(12) United States Patent
Hashiguchi (10) Patent No.: US 7,563,269 B2
(45) Date of Patent: Jul. 21, 2009

(54) ULTRASONIC TREATMENT DEVICE

(75) Inventor: Toshihiko Hashiguchi, Sagamihara (JP)

(73) Assignee: Olympus Corporation, Tokyo (JP)

( * ) Notice: Subject to any disclaimer, the term of this patent is extended or adjusted under 35 U.S.C. 154(b) by 780 days.

(21) Appl. No.: 10/751,564

(22) Filed: Jan. 5, 2004

(65) Prior Publication Data

US 2004/0193199 A1    Sep. 30, 2004

(30) Foreign Application Priority Data

Jan. 6, 2003    (JP) ............................. 2003-000613

(51) Int. Cl.
*A61B 17/28* (2006.01)
*A61B 17/42* (2006.01)
(52) U.S. Cl. ..................... 606/169; 606/205; 606/170
(58) Field of Classification Search ................ 606/169, 606/205, 207, 208, 206, 170, 174
See application file for complete search history.

(56) References Cited

U.S. PATENT DOCUMENTS 5,954,746 A * 9/1999 Holthaus et al. ............. 606/205
6,139,561 A * 10/2000 Shibata et al. ............... 606/169
6,165,191 A * 12/2000 Shibata et al. ............... 606/169

FOREIGN PATENT DOCUMENTS

| JP | 52-102082 | 1/1976 |
|---|---|---|
| JP | 07-241393 | 9/1995 |
| JP | 2000-197640 | 7/2000 |
| JP | 2001-57985 | 3/2001 |

* cited by examiner

*Primary Examiner*—Vy Q. Bui
(74) *Attorney, Agent, or Firm*—Scully, Scott, Murphy & Presser, P.C.

(57) ABSTRACT

An ultrasonic treatment device for surgery includes: a treatment portion (ultrasonic probe) for treating living-body tissue by transmitting thereto ultrasonic vibrations generated by means of an ultrasonic transducer; a fixed manipulating section main body wherein this treatment portion is inserted and arranged; a moveable jaw that grips living-body tissue with this treatment portion, being arranged opposite to this treatment portion and being freely rotatably supported at the peripheral surface of this manipulating section main body; and a moveable handle linked with the moveable jaw for opening/closure operation of this moveable jaw with respect to the treatment portion and freely rotatably supported on the peripheral surface of the manipulating section main body; wherein the moveable jaw and the moveable handle are arranged on the same side with respect to the longitudinal central axis of the fixed manipulating section main body.

14 Claims, 9 Drawing Sheets

FIG.10

ULTRASONIC TREATMENT DEVICE

This application claims benefit of Japanese Application No. 2003-000613 filed in Japan on Jan. 6, 2003, the contents of which are incorporated by this reference.

BACKGROUND OF THE INVENTION

1. Field of the Invention

The present invention relates to an ultrasonic treatment device employed in surgical operations upon abdominal section or upon insertion into a body cavity through a trocar or the like, and performing ultrasonic treatment such as incision, excision or coagulation of living-body tissues by gripping the living-body tissues.

2. Description of the Related Art

In general, ultrasonic treatment devices for medical use are treatment devices whereby ultrasonic treatment such as incision, excision or coagulation of living-body tissue is performed. Such ultrasonic treatment devices include treatment devices used for surgical operations employed when surgical operations are performed upon abdominal section or upon insertion into a body cavity through a trocar or the like.

Such an ultrasonic treatment device for surgical use is proposed in for example Laid-open Japanese Patent Publication No. 2000-197640 and Laid-open Japanese Patent Publication No. 2001-57985.

SUMMARY OF THE INVENTION

An ultrasonic treatment device according to the present invention comprises an ultrasonic probe for treating living-body tissue by transmitting thereto ultrasonic vibrations generated by means of an ultrasonic transducer; a manipulating section main body at a fixed side wherein this ultrasonic probe is inserted and arranged at the distal end thereof; a moveable jaw, arranged opposite to the ultrasonic probe, that grips living-body tissue with the ultrasonic probe, and that is freely rotatably supported at the peripheral surface of this manipulating section main body; a moveable handle linked with the moveable jaw for opening/closing operation of this moveable jaw with respect to the ultrasonic probe and freely rotatably supported at the peripheral surface of this manipulating section main body; wherein the moveable jaw and the moveable handle are arranged on the same side with respect to the longitudinal central axis of the manipulating section main body.

DESCRIPTION OF THE PREFERRED EMBODIMENTS

An embodiment of the present invention is described below with reference to the drawings.

Figure 1:
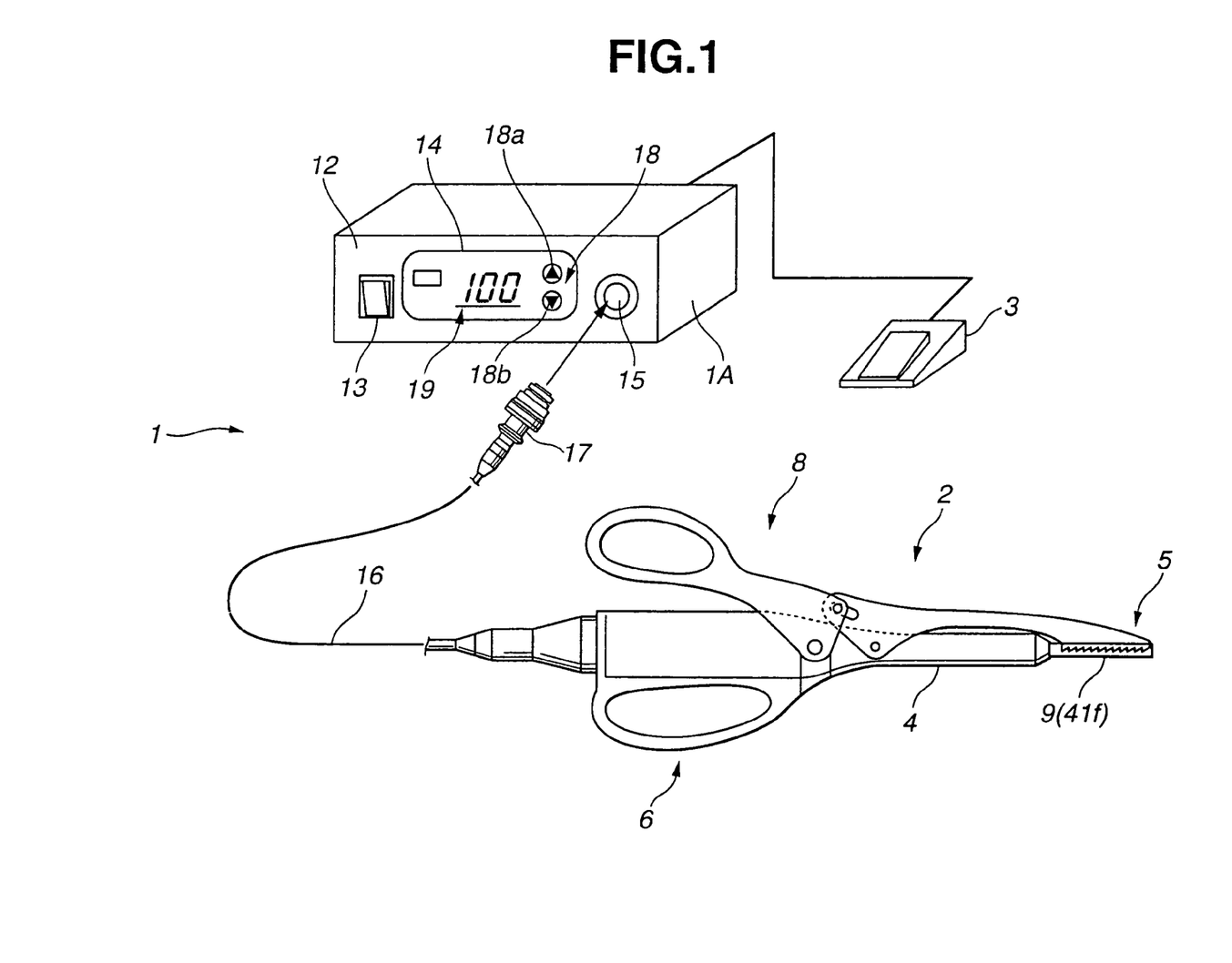
FIG. 1 is an overall constructional diagram showing an ultrasonic treatment device according to an embodiment of the present invention.
Figure 2:
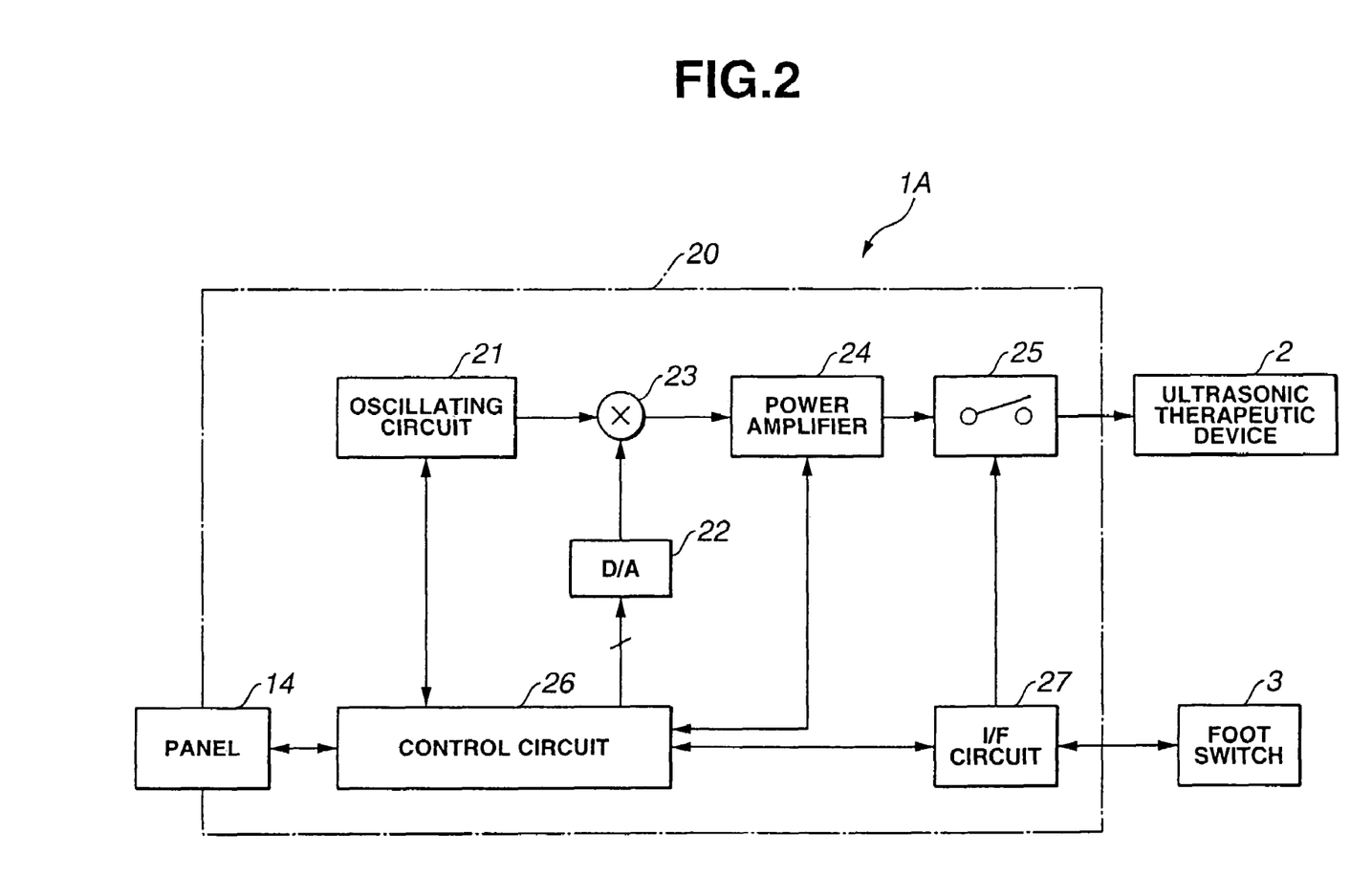
FIG. 2 is a circuit block diagram showing the construction of the device console of FIG. 1.
Figure 3:
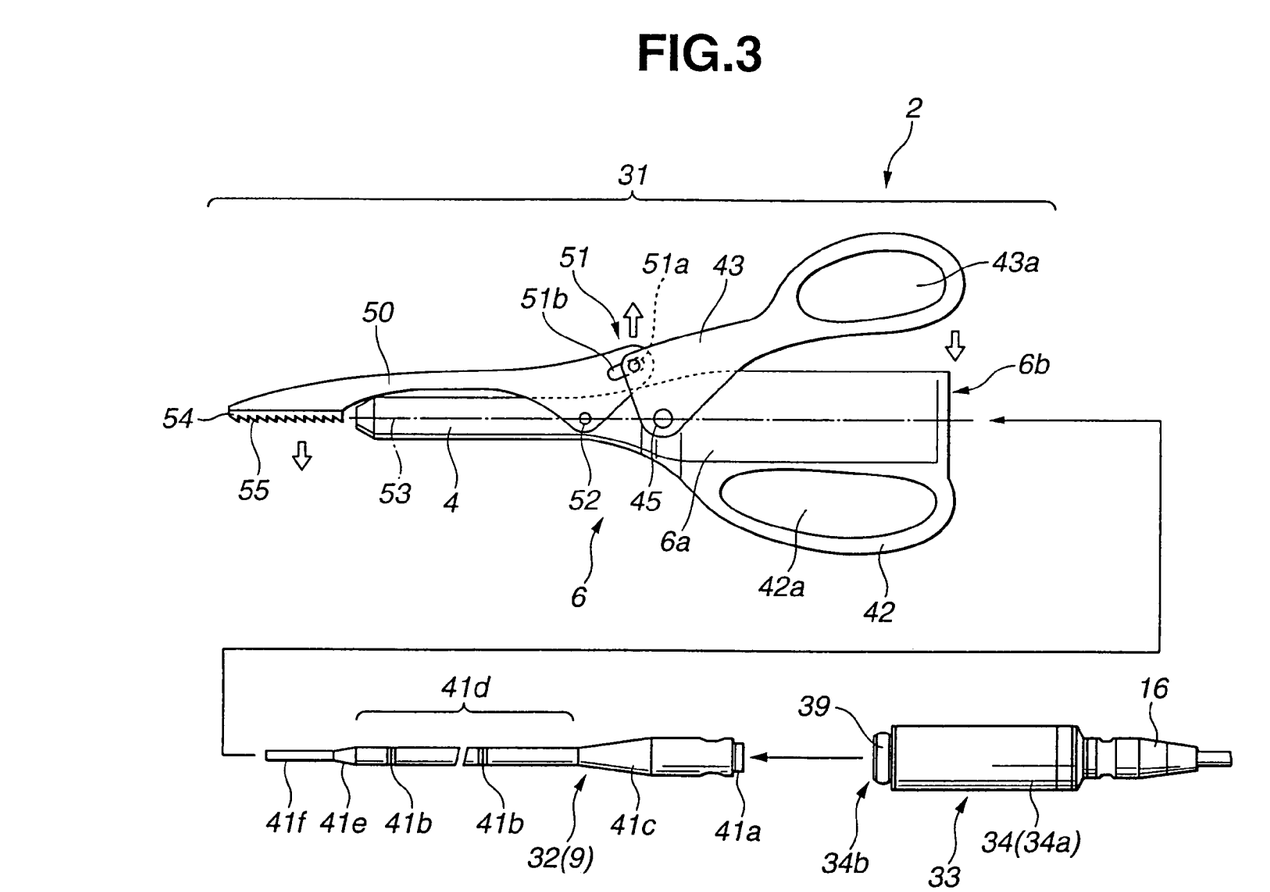
FIG. 3 is a side view shown in exploded fashion of the ultrasonic treatment instrument of FIG. 1.
Figure 4:
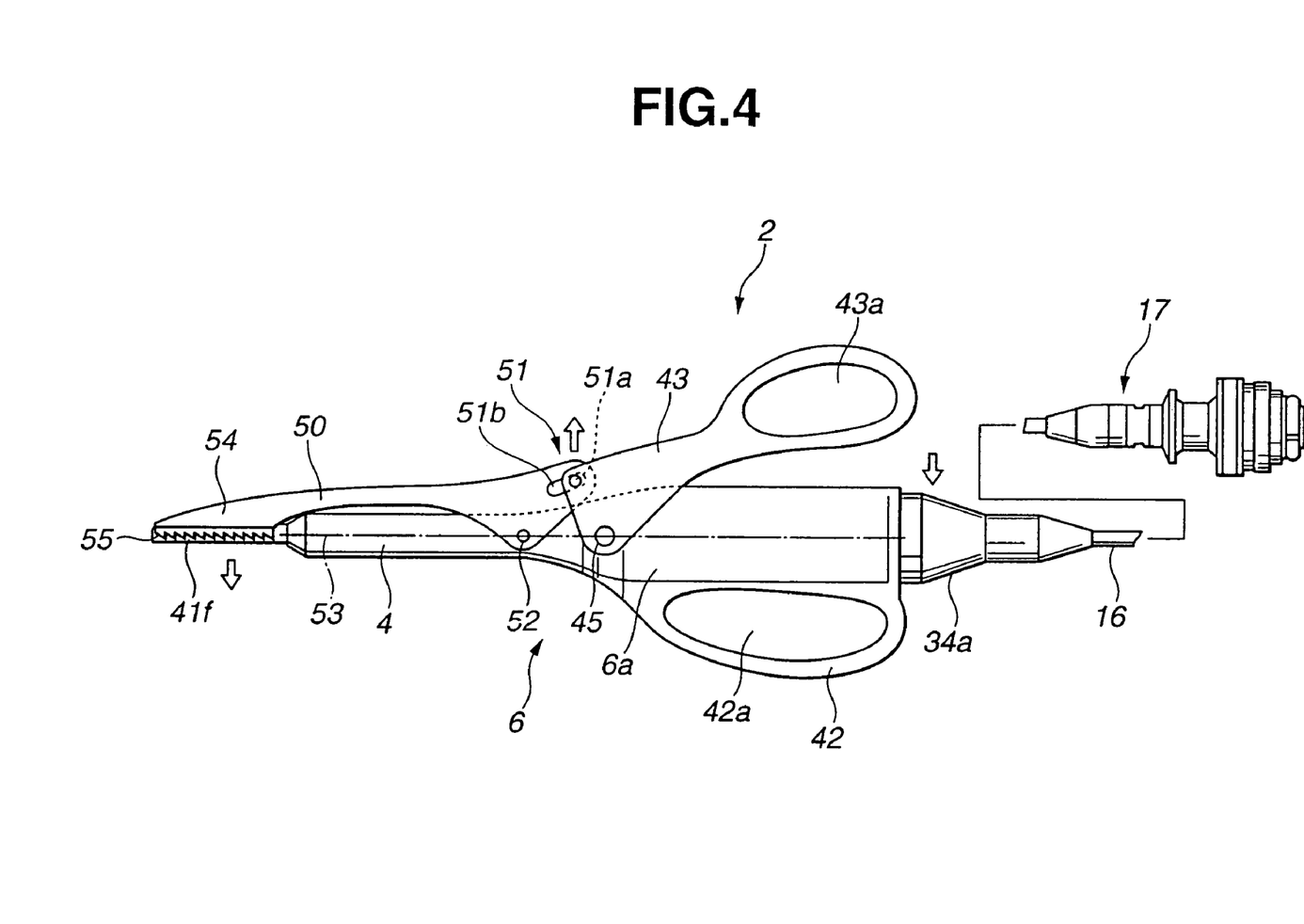
FIG. 4 is a side view showing the assembled condition of the ultrasonic treatment instrument of FIG. 1.
Figure 5:
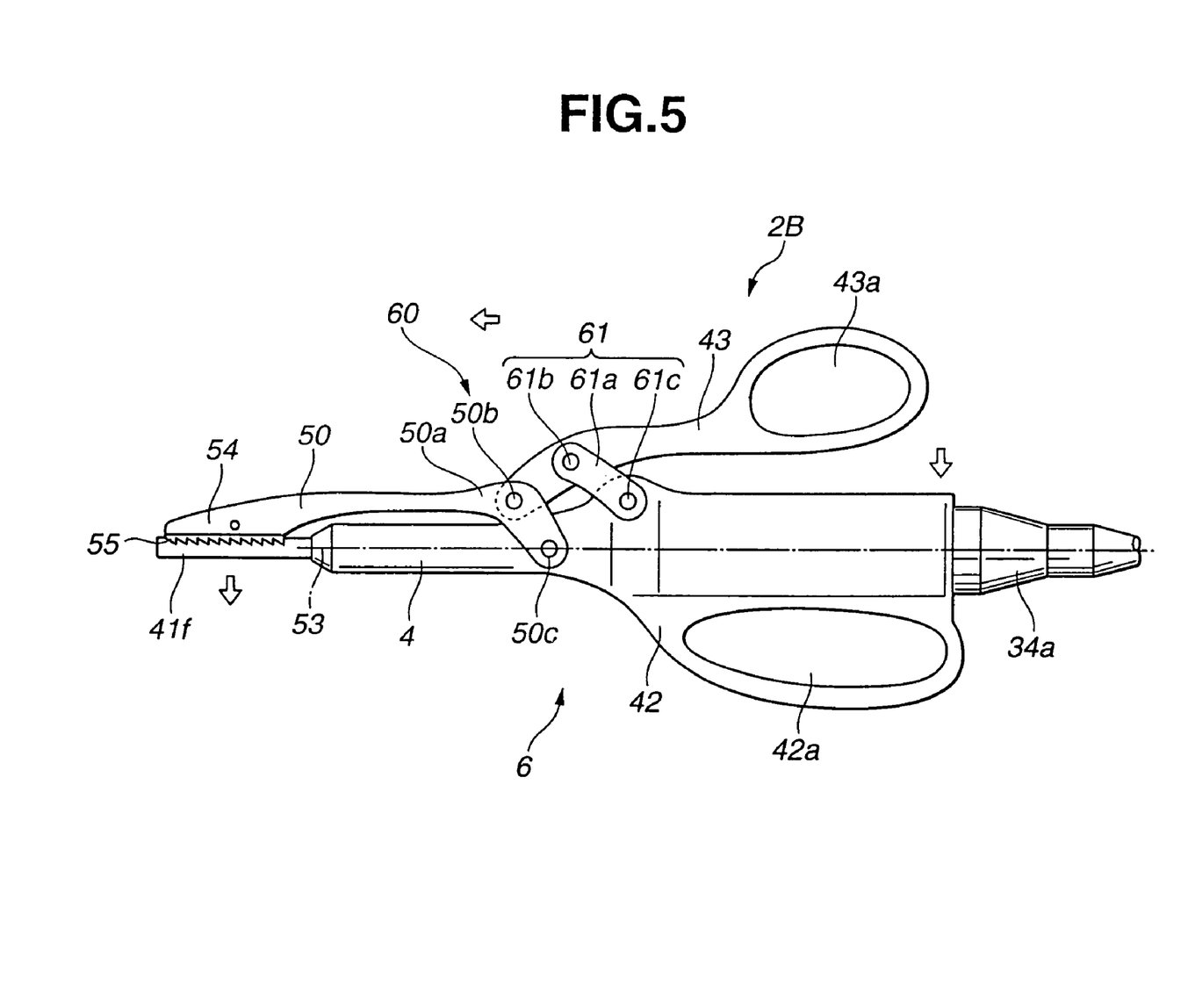
FIG. 5 is a side view of an ultrasonic treatment instrument showing a modified example.

FIG. 1 to FIG. 5 relate to an embodiment of the present invention. FIG. 1 is an overall constructional diagram showing an ultrasonic treatment device according to an embodiment of the present invention; FIG. 2 is a circuit block diagram showing the construction of the device console of FIG. 1; FIG. 3 is a side view shown in exploded fashion of the ultrasonic treatment instrument of FIG. 1; FIG. 4 is a side view showing the assembled condition of the ultrasonic treatment instrument of FIG. 1; FIG. 5 is a side view of an ultrasonic treatment instrument showing a modified example of the ultrasonic treatment device shown in FIG. 4.

As shown in FIG. 1, an ultrasonic treatment device 1 according to the present embodiment comprises an ultrasonic treatment instrument 2 for surgical operations and a foot switch 3 respectively connected with a device console 1A. The device console 1A is also capable of being connected with an ultrasonic treatment instrument 2 that is capable of insertion into a body cavity. The ultrasonic treatment instrument 2 is respectively provided with a treatment unit 5 at the distal end of an elongate sheath 4 and a manipulating section 6 on the side of the operator. The manipulating section 6 incorporates an ultrasonic transducer, not shown, that generates ultrasonic vibrations, and is also provided with an operating handle 8 whereby the treatment unit 5 may be controlled.

The sheath 4 is provided in its interior with a vibration-transmitting member 9 that transmits ultrasonic vibrations from the ultrasonic transducer to the treatment unit 5. The distal end of the vibration-transmitting member 9 is exposed outside the distal end of the sheath 4.

In addition, a control panel 12 is provided at the front face of the device console 1A. The control panel 12 is provided with a power source switch 13, a control display panel 14, and an ultrasonic treatment instrument connecting unit 15. The manipulating section 6 of the ultrasonic treatment instrument 2 is connected with one end of a handpiece cord 16. A handpiece plug 17 that is arranged at the other end of the handpiece cord 16 is detachably connected with the ultrasonic treatment instrument connecting unit 15 of the device console 1A.

The control display panel 14 of the device console 1A comprises setting switches 18 for setting the-magnitude of the ultrasonic output during ordinary operation when performing ultrasonic treatment, and a display 19 that provides a digital display of the magnitude of the ultrasonic output that is set by these setting switches 18. These setting switches 18 comprise an output increasing switch 18a that alters (increases/decreases) the magnitude of the ultrasonic output, and an output decreasing switch 18b.

In addition, as shown in FIG. 2, the device console 1A incorporates a drive circuit 20 for supplying electrical energy to the ultrasonic transducer in the ultrasonic treatment instrument 2.

The drive circuit 20 comprises an oscillation circuit 21 that generates an AC signal of ultrasonic frequency, a D/A converter 22 that generates a signal designating the magnitude of the ultrasonic output, a VCA circuit 23 that controls the magnitude of the AC signal of the oscillation circuit 21 based on a signal from the D/A converter 22, a power amplifier 24 that amplifies the output of the VCA circuit 23 and generates power that drives the ultrasonic transducer in the ultrasonic treatment instrument 23, a relay 25 that connects or disconnects the output line of the drive circuit 20, a control circuit 26 that controls the operation of the ultrasonic treatment device 1, and an interface (I/F) circuit 27 that transmits an operation signal from the foot switch 3 to the control circuit 26 and the relay 25.

The control circuit 26 also incorporates operating condition changeover means that, on commencement of ultrasonic treatment in response to operation of the foot switch 3, increases the ultrasonic output from the ultrasonic transducer in the ultrasonic treatment instrument 2 to be larger than the output value that is set by means of the setting switch 18 and that, at the time when a pre-set prescribed setting time has elapsed after commencement of ultrasonic treatment, controls the ultrasonic output from the ultrasonic transducer to a set output value. A relay 25 of the drive circuit 20 is interposed between the ultrasonic treatment instrument connecting unit 15 and a power amplifier 24.

As shown in FIG. 3 and FIG. 4, the ultrasonic treatment instrument 2 is capable of being disassembled into three units. Specifically, it comprises a handle unit 31, a probe unit 32 and a transducer unit 33. These three units 31 to 33 are assembled in the condition shown in FIG. 4.

The transducer unit 33 is provided with a handpiece 34 that is detachably connected with the handle unit 31. The handpiece 34 incorporates an ultrasonic transducer (not shown) for generating ultrasonic vibrations in a cylindrical cover 34a.

This ultrasonic transducer is connected at its distal end with a horn (not shown) that performs amplitude magnification; the distal end of the horn is mounted at the proximal end of the probe unit 32.

Also, the cylindrical cover 34a is provided at its distal end with a unit coupling section 34b that is detachably connected with a transducer connecting unit 6b of a manipulating section main body 6a, to be described, of the handle unit 31. A C-shaped connecting ring 39 (so-called C ring) formed by removing a part of a ring is mounted at the peripheral surface of the unit coupling section 34b. The coupling ring 39 is formed of a substantially half-moon shaped cross-section, the outer circumference of the coupling ring 39 being arcute.

In addition, a handpiece cord 16 provided with a handpiece plug 17 at its end is connected at the rear end of the cylindrical cover 34a.

Also, the probe unit 32 is provided with an elongate substantially rod-shaped vibration transmitting member 9 that is detachably connected with the distal end of the horn, not shown, in the transducer unit 33.

The proximal end of the vibration transmitting member 9 is formed with a mounting screw 41a that is connected with a probe mounting section of the horn, not shown. Also, the mounting screw 41a is screwed in and fixed in a screw-hole of the probe mounting section in the transducer unit 33. The probe unit 32 and transducer unit 33 are thereby integrally assembled.

Furthermore, the vibration transmitting member 9 is provided with a flange-shaped support body 41b at the positions of nodes (at a plurality of locations) of the standing wave of the ultrasonic vibrations transmitted from the proximal end. The support body 41b is formed as a ring-shaped resilient member.

Also, at the vibration transmitting member 9 of the present embodiment, in front of the second node from the proximal end, there is provided a proximal end-side horn 41c that performs a second stage of amplitude magnification. Furthermore, at the distal end of the proximal end-side horn 41c, there are provided, in order, an intermediate section 41d that performs transmission of ultrasonic vibrations, a distal end-side horn 41e that performs the final amplitude magnification and a treatment section 41f (ultrasonic probe). The treatment section 41f that is arranged at the distal most end of the vibration transmitting member 9 is formed in substantially circular cross-sectional shape.

The handle unit 31 comprises a sheath 4 and a manipulating section 6 arranged at the proximal end of the sheath 4. The manipulating section 6 of the handle unit 31 comprises a substantially cylindrical manipulating section main body 6a. At the proximal end of the manipulating section main body 6a, a transducer connecting unit 6b is formed.

In addition, the manipulating section main body 6a is a fixed side, and is provided with a fixed handle 42, on its peripheral surface, and a moveable handle 43 that is freely rotatable and that constitutes control means; the fixed handle 42 and the moveable handle 43 constitute an operating handle 8 (see FIG. 1). The manipulating section main body 6a may be provided with an electrode pin for high frequency electric current connection, to which a high frequency electric power supply device, not shown, is connected. In this case, the sheath 4 may be fitted with an insulating tube, not shown. Alternatively, the sheath 4, manipulating section 6, fixed handle 42, moveable handle 43 and moveable jaw 50 may be formed of plastic.

Also, the fixed handle 42 is integrally formed with the cylindrical manipulating section main body 6a. A manipulating end of the fixed handle 42 is provided with finger engagement holes 42a for selective insertion of a plurality of fingers other than the thumb; a manipulating end of the moveable handle 43 is likewise provided with a thumb engagement hole 43a for engagement of the thumb of the same hand.

Also, the moveable handle 43 is freely rotatably supported by means of a pivot shaft 45 at the peripheral surface of the manipulating section main body 6a. At the distal end of the moveable handle 43, the proximal end of the moveable jaw 50 is connected by means of a cam mechanism 51.

The cam mechanism 51 is constituted by a cam pin 51a projecting at the distal end of the moveable handle 43 and a cam groove 51b formed at the proximal end of the moveable jaw 50, with which the cam pin 51a of the moveable handle 43 is freely engaged.

The moveable jaw 50 is freely rotatably supported by means of a pivot shaft 52 at the peripheral surface of the manipulating section main body 6a. The moveable handle 43 and the moveable jaw 50 are arranged on the same side of the longitudinal central axis 53 of the manipulating section 6.

Also, the moveable jaw 50 is arranged to be capable of being opened or closed by rotation in the vertical direction with respect to handle operation of the moveable handle 43. The moveable jaw 50 is provided with a gripping member 54 at its distal end. The gripping member 54 is formed with substantially sawtooth shaped teeth 55. The gripping member 54 is formed by low-friction material such as for example PTFE (Teflon: trademark of Dupont Inc). Also, since the gripping member 54 on its own is lacking in rigidity, rigidity may be ensured by mounting a metal strengthening member, not shown.

Also, the gripping member 54 and the treatment portion 41f of the vibration transmitting member 9 are in contact over a wide area, thereby making it possible to raise gradually the temperature over a wide area of the living-body tissue that is clamped therebetween and so enabling effective coagulation to be achieved. Since the gripping face of the gripping member 54 and the treatment portion 41f of the vibration transmitting member 9 are brought into contact at the respective arcuate curved surfaces thereof, their centers naturally coincide and it is a benefit. In this way, eccentricity or tilting of the treatment portion 41f of the ultrasonic treatment instrument 2 can be cancelled.

With the ultrasonic treatment instrument 2 according to this embodiment, when a closure operation is performed on the moveable handle 43, upwardly directed force is applied at the distal end of the moveable handle 43, by using the pivot shaft 45 of the moveable handle 43 as a fulcrum and upwardly directed force is applied to the proximal end of the moveable jaw 50 that is connected thereto by the cam mechanism 51. Thus, downwardly directed force is applied to the distal end of the moveable jaw 50 by using the pivot shaft 52 as a fulcrum, thereby effecting closure with the treatment portion 41f. When an operation of opening the moveable handle 43 is performed, the ultrasonic treatment instrument 2 performs the opposite action to the closure operation described above.

Thus, during closure operation of the moveable jaw 50, the living-body tissue is gripped between the treatment portion 41f and the gripping member 54 of the moveable jaw 50, by pressing the gripping member 54 of the moveable jaw 50 onto the treatment portion 41f of the probe unit 32. Ultrasonic treatment such as coagulation or incision is then performed on the living-body tissue that is thereby gripped, with frictional heating between the living-body tissue and the treatment portion 41f that vibrates at high speed. The moveable jaw 50 may also be employed for exfoliating living-body tissue.

The ultrasonic treatment device 1 constructed in this way is employed when surgical operations are performed upon abdominal section or upon insertion into a body cavity through a trocar or the like and ultrasonic treatment such as incision, excision or coagulation of living-body tissues is performed by gripping the living-body tissues. The surgeon manipulates the moveable handle 43 while gripping the fixed handle 42 of the handle unit 31. Force in the vertical direction is then applied to the pivot shaft 52 of the moveable jaw 50 by the action of the cam mechanism 51 by manipulation of the handle of the moveable handle 43, causing the moveable jaw 50 to open or close with respect to the treatment portion 41f.

The surgeon then performs a closure operation on the moveable handle 43 while gripping the handle. The surgeon then grips the manipulating section main body 6a using his palm with four fingers engaged with finger engagement holes 42a of the fixed handle 42 and performs opening/closure operation of the moveable jaw 50 by engagement of his thumb with the thumb engagement hole 43a of the moveable handle 43.

When doing this, upwardly directed force is applied to the distal end of the moveable handle 43 of the ultrasonic treatment instrument 2, by using the pivot shaft 45 of the moveable handle 43 as a fulcrum and upwardly directed force is applied to the proximal end of the moveable jaw 50 that is connected thereto by the cam mechanism 51. Operation in the direction such as to effect closure with the treatment portion 41f of the ultrasonic treatment instrument 2 is then performed by application of downwardly directed force to the distal end of the moveable jaw 50 by using the pivot shaft 52 as a fulcrum.

The living-body tissue is then gripped between the moveable jaw 50 and the treatment portion 41f by pressing of the gripping member 54 onto the treatment portion 41f of the probe unit 32. The surgeon then performs ultrasonic treatment of the living-body tissue that is thus gripped by depressing the foot switch 3.

Ultrasonic treatment of the living-body tissue that is thus gripped is performed with the frictional heating between the living-body tissue and the treatment portion 41f that is vibrated at high speed. As a result, the ultrasonic treatment device 1 is of simple construction and is easy to operate and opening/closure of the moveable jaw 50 can be performed by opening/closure operation of the moveable handle 43.

The ultrasonic treatment instrument of the ultrasonic treatment device 1 may be constructed as shown in FIG. 5.

As shown in FIG. 5, an ultrasonic treatment instrument 2B according to this modified example is constructed with the moveable handle 43 and the moveable jaw 50 supported on the same side of the longitudinal central axis 53 of the manipulating section main body 6a, a link mechanism 60 being provided instead of the cam mechanism 51.

A backward link 61 of the link mechanism 60 is constituted such that a backward link 61 supports the distal end of the moveable handle 43 so as to freely rotatable on the peripheral surface of the manipulating section main body 6a and an extension 50a of the moveable jaw 50 extending on the proximal end thereof is constituted and supported in a freely rotatable manner on the peripheral surface of the manipulating section main body 6a, being linked with the distal end of the moveable handle 43.

A link member 61a of the backward link 61 is supported by a handle-side pivot shaft 61b on the moveable handle 43 and also is supported by a support shaft 61c on the main body side at the peripheral surface of the manipulating section main body 6a. Furthermore, the extension 50a of the moveable jaw 50 is supported by a jaw-side pivot shaft 50b at the distal end of the moveable handle 43 and is supported by a pivot shaft 50c on the main body side, at the peripheral surface of the manipulating section main body 6a.

In the ultrasonic treatment instrument 2B of this modified example, when the moveable handle 43 is subjected to opening/closure operation by gripping the handle, force in the forward/backward direction is applied to the pivot shaft 61c on the main body side through the handle-side pivot shaft 61b of the backward link 61, causing the link mechanism 60 to be actuated so as to move the moveable handle 43 in the forward/backward direction. In addition, the construction is such that, accompanying the movement of the moveable handle 43 in the forward/backward direction, the extension 50a of the moveable jaw 50 applies force in the forward/backward direction to the main-body side pivot shaft 50c through the jaw-side pivot shaft 50b, thereby opening/closing the moveable jaw 50 with respect to the treatment portion 41f.

Specifically, in the ultrasonic treatment instrument 2B, when an opening operation of the moveable handle 43 is performed, upwardly directed force is applied to the handle-side pivot shaft 61b of the backward link 61, with the result that the link member 61a is rotated clockwise and the moveable handle 43 is moved in the backward direction. In addition, accompanying this movement of the moveable handle 43 in the backward direction, the extension 50a of the moveable jaw 50 applies force in the backward direction to the main-body side pivot shaft 50c through the jaw-side pivot shaft 50b, causing the moveable jaw 50 to open with respect to the treatment portion 41f. It should be noted that the ultrasonic treatment instrument 2B is arranged so as to perform an action opposite to the case described above wherein an opening operation is performed, when a closure operation of the moveable handle 43 is performed.

Thus, the same benefits as in the case of the ultrasonic treatment instrument 2 can be obtained with the ultrasonic treatment instrument 2B of this modified example.

Incidentally, the prior art ultrasonic treatment instrument is formed with a jaw either of the same width as the total width of the gripping member or narrower than the gripping member. Consequently, with the prior art ultrasonic treatment instrument, there is a risk that the gripping member may not effectively perform a close contact to the living-body tissue that is gripped between itself and the ultrasonic probe, due to resilient deformation of both sides of the jaw. Also, with the prior art ultrasonic treatment instrument, the construction of the portion whereby the gripping member is mounted on to the jaw is complicated.

An ultrasonic treatment instrument is therefore sought wherein mounting onto the jaw is simple and comprising a gripping member of improved close contact.

Figure 6:
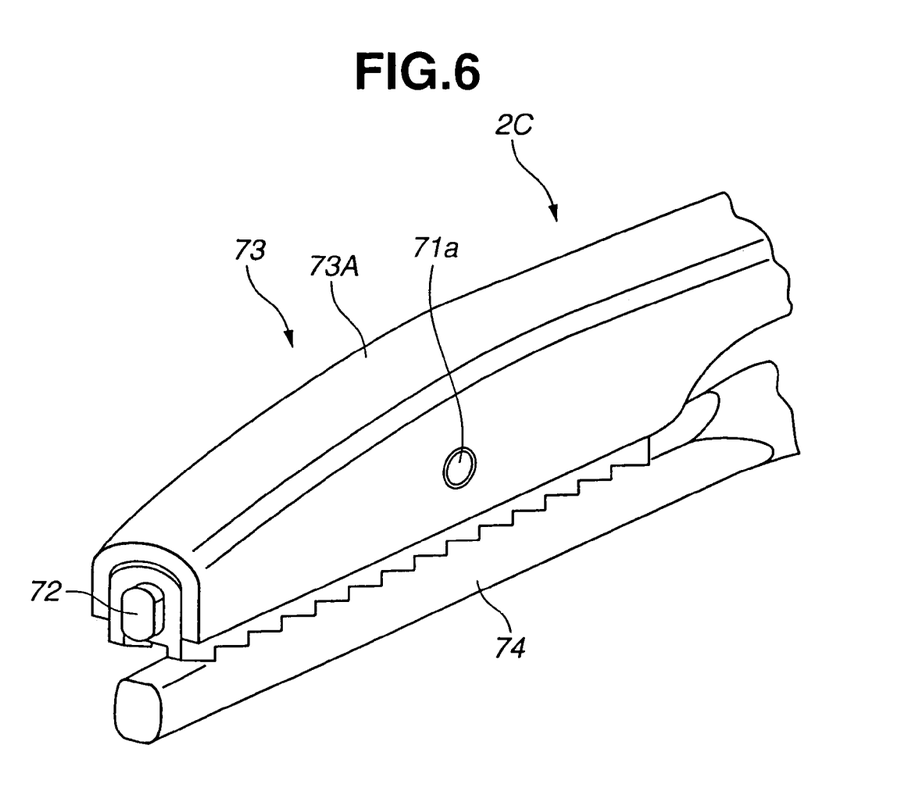
FIG. 6 is a detail view to a larger scale of an ultrasonic treatment instrument comprising a gripping member of improved close contact that can be mounted on the jaw in a simple fashion.
Figure 7:
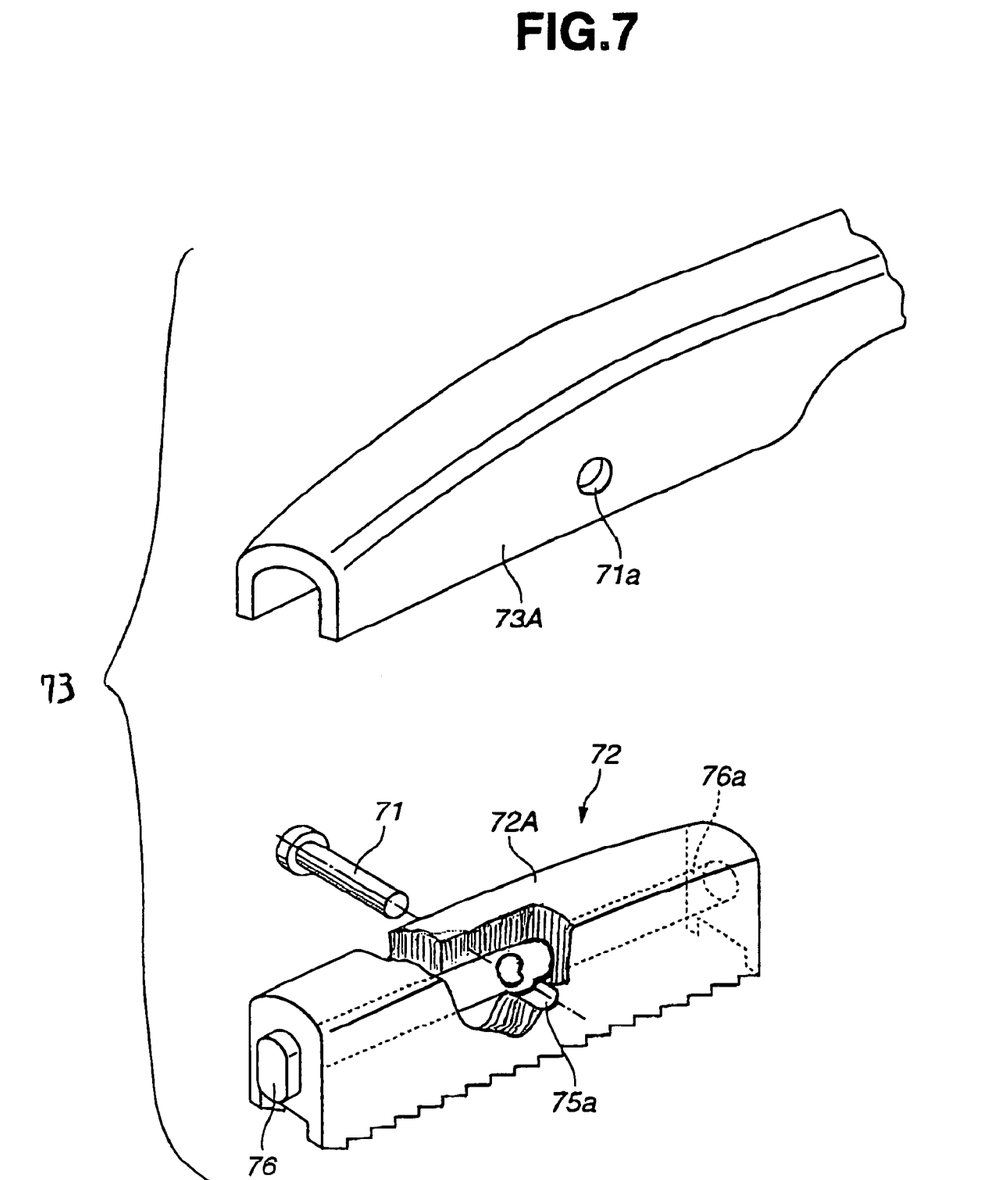
FIG. 7 is a diagram shown in exploded fashion of the ultrasonic treatment device of FIG. 6.

FIG. 6 and FIG. 7 show the construction of an ultrasonic treatment instrument comprising a gripping member of improved close contact wherein mounting onto the jaw is simple, FIG. 6 being a detailed view to a larger scale of the ultrasonic treatment instrument and FIG. 7 being a diagram showing an exploded condition of FIG. 6.

In the ultrasonic treatment instrument 2C shown in FIG. 6, a jaw 73 integrally comprises a jaw body 73A in such a manner to house a gripping member 72 that is held in rockable fashion at pivot holes 71a by means of a pivot shaft 71. In the meantime, a number 74 is the ultrasonic probe.

Also, the jaw 73 may be constructed with the gripping member 72 mounted on the jaw body 73A in rockable fashion in accordance with the living-body tissue that is gripped.

As shown in FIG. 7, the jaw body 73A is formed in substantially U shape so as to cover the gripping member 72, and pivot holes 75a are formed, through which a pivot shaft 71 passes in the vicinity of the middle thereof.

Furthermore, in the gripping member 72, a rigidity-increasing member 76 made of metal is inserted into and arranged extending in a hole 76a formed in the longitudinal direction in a gripping section body 72A thereof made of plastic, and is formed with pivot holes 75a through which a pivot shaft 71 passes in the vicinity of the middle thereof.

In this way, rigidity of the gripping member 72 is ensured by the arrangement of the rigidity-increasing member 76 in a portion that otherwise makes little contribution to rigidity, namely, in the vicinity of the center of the cross-sectional shape thereof. Also, the jaw 73 is covered by the gripping member 72 and is constructed so as to hold the gripping member 72 in rockable fashion by means of the pivot shaft 71.

In this way, high rigidity of the gripping member 72 of the ultrasonic treatment instrument 2C is ensured, and effective close contact with respect to the living-body tissue that is gripped between the gripping member and the ultrasonic probe 74 is thereby made possible over the entire width. Also, mounting of the gripping member 72 onto the jaw 73 of the ultrasonic treatment instrument 2C is simple, so manufacture is easily accomplished.

Furthermore, since the metal portions that are exposed at the outer surface of the gripping member 72 are extremely small, the benefit is obtained in that the possibility of sticking of living body tissue burnt due to the heat to the metal portions is decreased, facilitating washing and cleaning. Also, in this example, the cross-sectional (front face) shape of the treatment portion 41f is substantially rectangular. As a result, rigidity of the ultrasonic treatment instrument 2C in the vertical direction is improved and the energy density of the gripping face is increased.

By the way, in the prior art ultrasonic treatment instrument, easiness of assembly of the sheath where the vibration transmission member is inserted and arranged and the proximal end of the moveable jaw 73 is poor, resulting in the implement tending to become bulky. This made the prior art ultrasonic treatment instrument difficult to operate. Also, in general, it is necessary to wash and clean the ultrasonic treatment instrument after use, the interior of the sheath being washed and cleaned with a brush.

However, in the prior art ultrasonic treatment device, cleaning is laborious, since the sheath is hollow so that washing and cleaning has to be performed by inserting a brush into the interior of the sheath.

An ultrasonic treatment instrument is therefore sought which should be of a simple construction, with a slim distal end and easy to operate.

Figure 8:
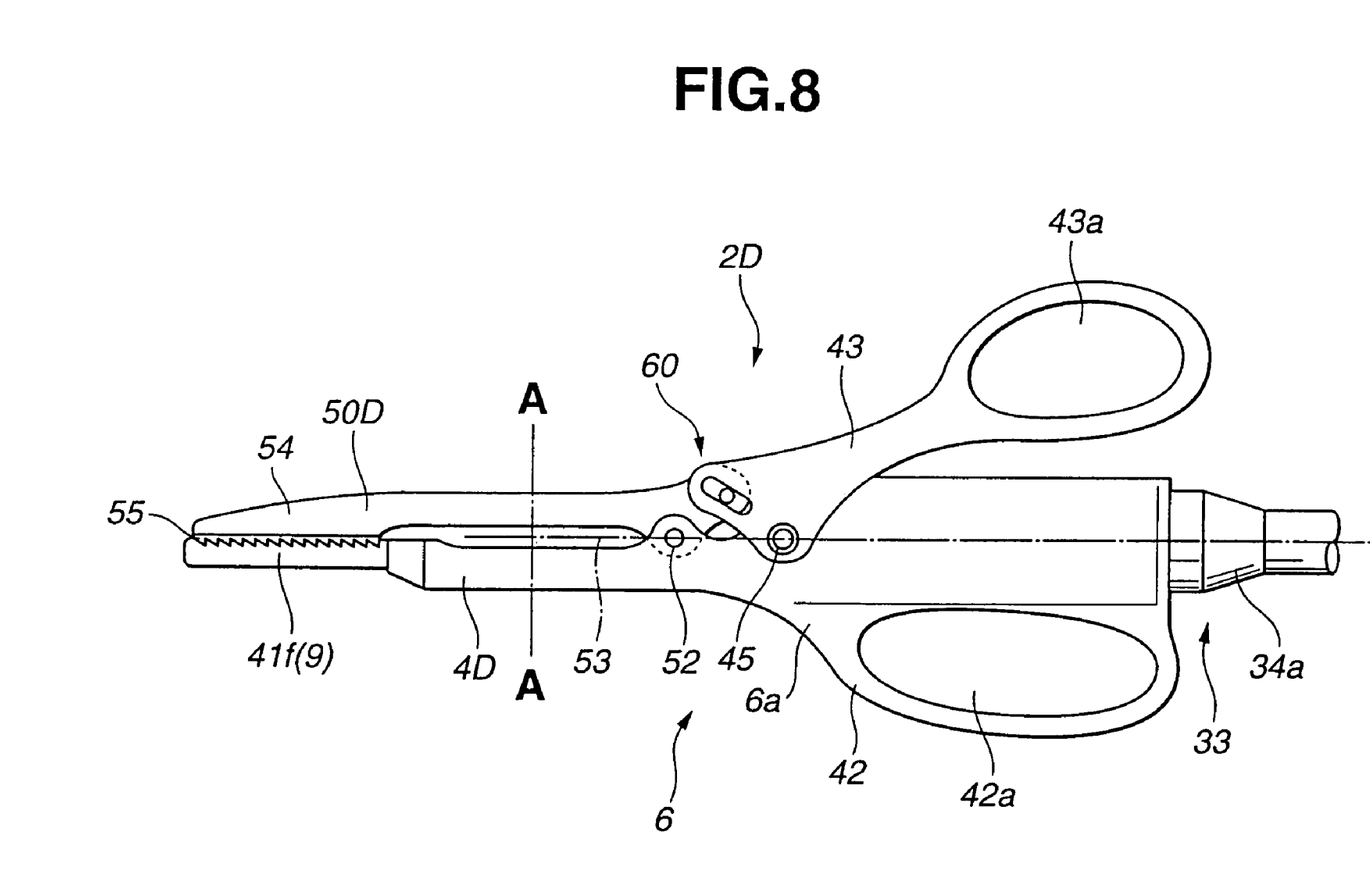
FIG. 8 is a side view showing an ultrasonic treatment instrument with a slim distal end and which is of simple construction.
Figure 9:
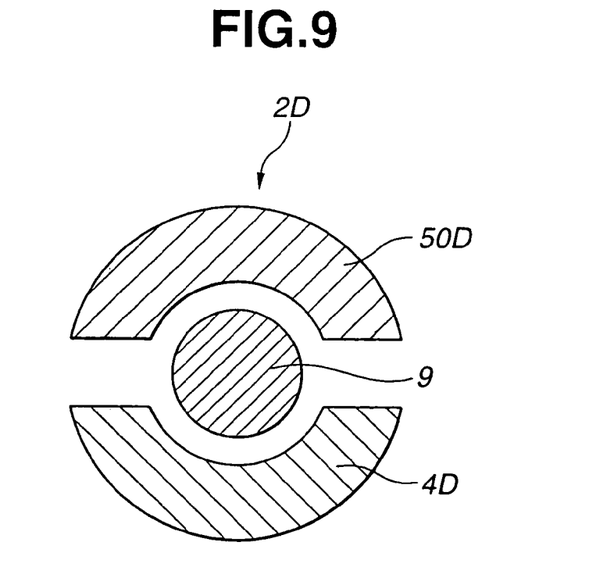
FIG. 9 is a sectional view along the line A-A of FIG. 8.
Figure 10:
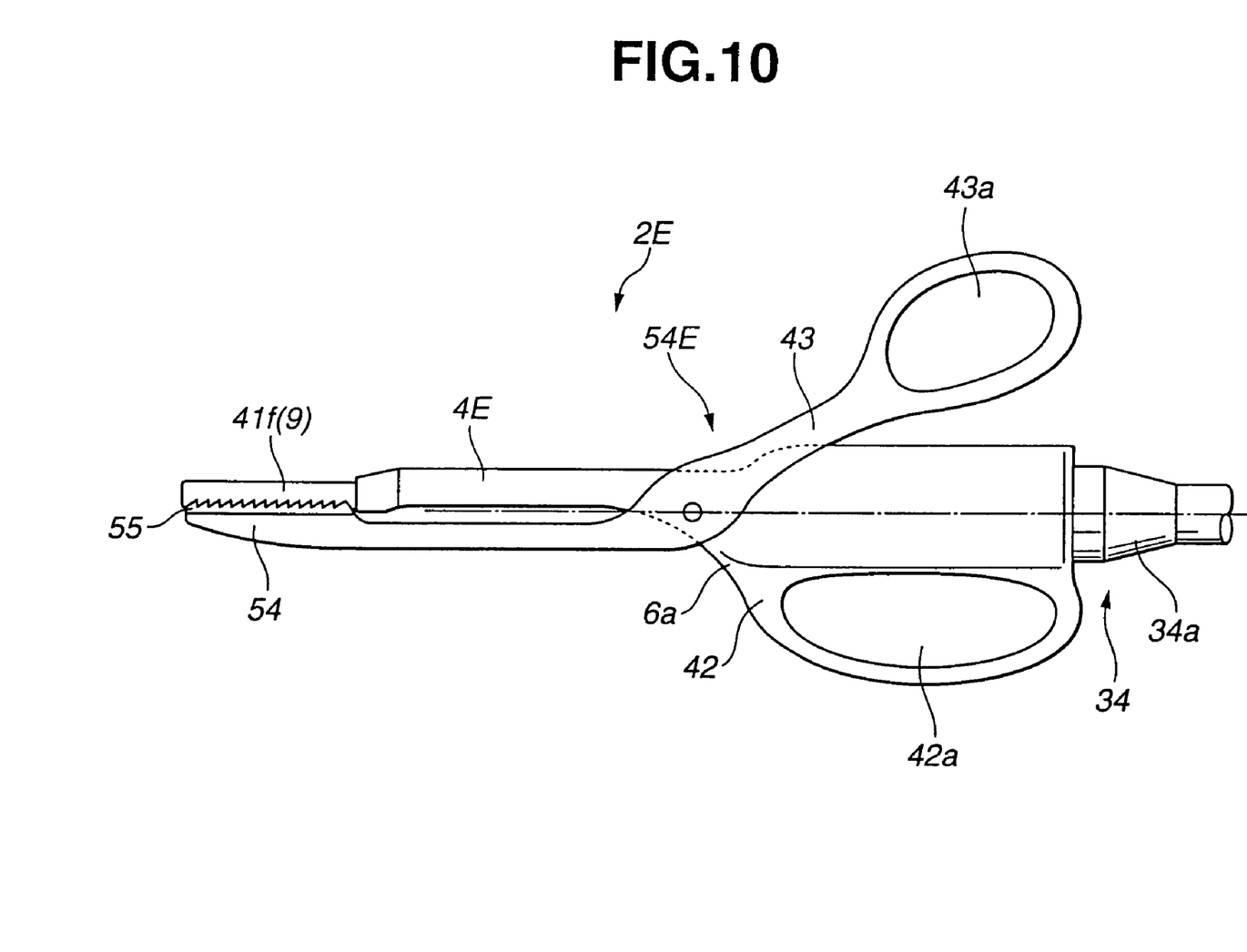
FIG. 10 is a side view of an ultrasonic treatment instrument showing a modified example in respect of the ultrasonic treatment device shown in FIG. 8.

FIG. 8 to FIG. 10 show the construction of an ultrasonic treatment instrument which is of a simple construction, with a slim distal end. FIG. 8 is a side view showing the ultrasonic treatment instrument, FIG. 9 is a sectional view of FIG. 8 along the line A-A and FIG. 10 is a side view of an ultrasonic treatment instrument showing an example of a modification of FIG. 8.

As shown in FIG. 8, in the ultrasonic treatment instrument 2D, just as is described with reference to the first embodiment, the moveable handle 43 and moveable jaw 50D are constructed being attached to the same side of the longitudinal central axis 53 of the manipulating section main body 6a by means of a cam mechanism 60.

Also, as shown in FIG. 9, in the ultrasonic treatment instrument 2D, the proximal end of the moveable jaw 50D is formed in an open construction of substantially arcuate cross-sectional shape and the distal end of the sheath 4D is formed in an open construction of substantially arcuate cross-sectional shape so as to match the proximal end of the moveable jaw 50D. Also, in this embodiment, the moveable jaw 50D and the sheath 4D are formed in semi-circular cross-sectional shape in the direction orthogonal to the longitudinal central axis 53.

Also, in the ultrasonic treatment instrument 2D, a vibration transmitting member 9 is inserted and arranged in a substantially circular-shaped compact space formed by the sheath 4D and the moveable jaw 50D.

Thus, since a construction of the ultrasonic treatment instrument 2D is adopted in which the vibration transmitting member 9 is inserted in the interior of a sheath 4D and moveable jaw 50D of substantially symmetrical cross-sectional shape, the external shape is slim so that the field of view and ease of operation in the surgical field are excellent and manufacture is easy.

Also, in the ultrasonic treatment instrument 2D, since the sheath 4D is opened to the outside after removal of the transducer unit 33, washing and cleaning are facilitated and it is easy to check for residual contamination.

The construction of the ultrasonic treatment instrument 2E shown in FIG. 10 is the same in this respect.

In the ultrasonic treatment instrument 2E, the moveable handle 43 is integrally formed as a moveable jaw 50E by extension as far as the distal end and the moveable jaw 50E are attached and constructed so as to be freely rotatable by means of a pivot shaft 45E at the proximal end of the sheath 4E. Also, in the ultrasonic treatment instrument 2E, the gripping member 54 is arranged on the opposite side of the moveable handle 43.

In this ultrasonic treatment instrument 2E also, in the same way as in the case of the ultrasonic treatment instrument 2D described above, the proximal end of the moveable jaw 50E is formed in a structure of. substantially arcuate open cross-sectional shape and the distal end of the sheath 4E is formed in an open substantially arcuate cross-sectional shape so as to match the proximal end of the moveable jaw 50E and a vibration transmitting member 9 is inserted and arranged in a substantially circular-shaped compact space formed by the sheath 4E and moveable jaw 50E.

In this way, the same benefits as in the case of the ultrasonic treatment instrument.2D can be obtained with the ultrasonic treatment instrument 2E also.

Having described preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasonic treatment device comprising:
    an ultrasonic probe for treating living-body tissue by transmitting thereto ultrasonic vibrations generated by means of an ultrasonic transducer;
    a manipulating section main body wherein the ultrasonic probe is inserted and arranged at the distal end thereof;
    a moveable jaw, arranged opposite to the ultrasonic probe, that grips living-body tissue with the ultrasonic probe, and that is supported to freely pivot about a first pivot shaft as a fulcrum at the peripheral surface of the manipulating section main body; and
    a moveable handle directly linked with the moveable jaw for opening/closure operation of the moveable jaw with respect to the ultrasonic probe and supported to freely pivot about a second pivot shaft as a fulcrum at the peripheral surface of the manipulating section main body,
    wherein the moveable jaw and the moveable handle are arranged on the same side with respect to the longitudinal central axis of the manipulating section main body.

2. The ultrasonic treatment device according to claim 1 comprising a drive circuit for driving the ultrasonic transducer.

3. The ultrasonic treatment device according to claim 2, wherein the drive circuit comprises a changeover unit that performs control that, on commencement of ultrasonic treatment, sets the ultrasonic output from the ultrasonic transducer to be larger than a set value set by a setting switch and that, when a pre-set prescribed time has elapsed after commencement of ultrasonic treatment, makes the ultrasonic output from the ultrasonic transducer to be a set value.

4. The ultrasonic treatment device according to claim 1, wherein the ultrasonic treatment device is separable into three units, namely: a handle unit comprising a sheath and a manipulating section main body formed at the proximal end of the sheath, a moveable jaw and a moveable handle; an ultrasonic probe unit; and a transducer unit internally having an ultrasonic transducer, and the ultrasonic treatment device is constituted so as to assemble the three units by incorporating the probe unit into the transducer unit and incorporating the transducer unit internally having the probe unit into the manipulating section main body of the handle unit.

5. The ultrasonic treatment device according to claim 4, wherein a fixed handle is provided at the periphery of the manipulation section main body.

6. The ultrasonic treatment device according to claim 1, constructed such that the moveable jaw is closed with respect to the ultrasonic probe by closure operation of the moveable handle.

7. The ultrasonic treatment device according to claim 1, wherein the moveable handle is rotatably supported by a pivot shaft at the peripheral surface of the manipulating section main body and the distal end of the moveable handle is linked by a cam mechanism or link mechanism with the proximal end of the moveable jaw.

8. The ultrasonic treatment device according to claim 4, wherein the probe unit comprises an elongated substantially rod-shaped vibration transmitting member and the moveable jaw comprises a gripping member at the distal end thereof and the gripping surface of the gripping member and the treatment portion of the vibration transmitting member are brought into contact at respective arcuate curved surfaces thereof.

9. The ultrasonic treatment device according to claim 8, wherein the gripping member and the treatment portion of the vibration transmitting member are formed so as to make contact over a wide area.

10. The ultrasonic treatment device according to claim 8, wherein the gripping member is formed by low-friction material.

11. The ultrasonic treatment device according to claim 1, frirther comprising a vibration transmitting member that transmits ultrasonic vibrations generated by the ultrasonic transducer to the ultrasonic probe, and a sheath that covers the vibration transmitting member,
    wherein the proximal end of the moveable jaw is formed in a substantially arcuate cross-sectional shape and the distal end of the sheath is formed in substantially arcuate cross-sectional shape so as to match the proximal end of the moveable jaw, the vibration transmitting member being arranged in a space between the moveable jaw and the sheath.

12. An ultrasonic treatment device comprising:
    a vibration transmitting member connected to an ultrasonic transducer, for transmitting ultrasonic vibrations generated by the ultrasonic transducer to the distal end thereof;
    an ultrasonic probe connected to the distal end of the vibration transmitting member, for treating living-body tissue by means of ultrasonic vibrations transmitted from the vibration transmitting member;
    a sheath that covers the vibration transmitting member;
    a manipulating section main body arranged at the proximal end of the sheath and in which the ultrasonic probe is inserted and arranged;
    a moveable jaw that grips living-body tissue with the ultrasonic probe, being arranged opposite to the ultrasonic probe and being supported to pivot freely about a first pivot shaft as a fulcrum on the peripheral surface of the manipulating section main body; and
    a moveable handle directly linked with the moveable jaw for opening/closure operation of the moveable jaw with respect to the ultrasonic probe and supported to pivot freely about a second pivot shaft as a fulcrum at the peripheral surface of the manipulating section main body;
    wherein while the proximal end of the moveable jaw is formed in substantially arcuate cross-sectional shape and the distal end of the sheath is formed in substantially arcuate cross- sectional shape so as to match the proximal end of the moveable jaw and the vibration transmitting member is arranged in a space between the sheath and moveable jaw, the moveable jaw and the moveable handle are arranged on the same side with respect to the longitudinal central axis of the manipulating section main body.

13. the ultrasonic treatment device according to claim 12, farther comprising a drive circuit for control drive of the ultrasonic transducer.

14. The ultrasonic treatment device according to claim 13, wherein the drive circuit comprises a changeover unit that performs control that, on commencement of ultrasonic treatment, sets the ultrasonic output from the ultrasonic transducer to be larger than a set value set by a setting switch and that, when a pre-set prescribed time has elapsed after commencement of ultrasonic treatment, makes the ultrasonic output from the ultrasonic transducer to be a set value.

* * * * *